(12) United States Patent
Folan et al.

(10) Patent No.: US 11,980,343 B2
(45) Date of Patent: May 14, 2024

(54) DEVICES AND METHODS FOR EXTENDING A WORKING CHANNEL

(71) Applicant: Boston Scientific Scimed Inc., Maple Grove, MN (US)

(72) Inventors: Martyn G. Folan, Loughrea (IE); Matthew Montague, Oranmore (IE); Louis McNern, Donegal (IE)

(73) Assignee: Boston Scientific Scimed Inc., Maple Grove, MN (US)

(*) Notice: Subject to any disclaimer, the term of this patent is extended or adjusted under 35 U.S.C. 154(b) by 0 days.

(21) Appl. No.: 17/977,594

(22) Filed: Oct. 31, 2022

(65) Prior Publication Data

US 2023/0059972 A1 Feb. 23, 2023

Related U.S. Application Data

(62) Division of application No. 16/379,051, filed on Apr. 9, 2019, now abandoned.

(60) Provisional application No. 62/655,975, filed on Apr. 11, 2018.

(51) Int. Cl.
*A61B 1/00* (2006.01)
*A61B 1/018* (2006.01)

(52) U.S. Cl.
CPC ...... *A61B 1/00119* (2013.01); *A61B 1/00066* (2013.01); *A61B 1/00105* (2013.01); *A61B 1/00121* (2013.01); *A61B 1/00128* (2013.01); *A61B 1/0014* (2013.01); *A61B 1/00147* (2013.01); *A61B 1/018* (2013.01)

(58) Field of Classification Search
CPC .............. A61B 1/00121; A61B 1/0014; A61B 1/00105; A61B 1/00066
See application file for complete search history.

(56) References Cited

U.S. PATENT DOCUMENTS

| | | | |
|---|---|---|---|
| 4,249,541 A | | 2/1981 | Pratt |
| 4,886,049 A | * | 12/1989 | Darras ............... A61B 1/00142 600/125 |
| 5,846,181 A | * | 12/1998 | Heckele ........... A61B 17/06109 600/114 |
| 6,520,954 B2 | | 2/2003 | Ouchi |
| 6,585,639 B1 | | 7/2003 | Kotmel et al. |
| 7,056,293 B2 | | 6/2006 | Reeves et al. |
| 7,775,968 B2 | | 8/2010 | Mathis |
| 7,927,271 B2 | | 4/2011 | Dimitriou et al. |
| 8,075,476 B2 | | 12/2011 | Vargas |
| 9,033,865 B2 | | 5/2015 | Suda |

(Continued)

FOREIGN PATENT DOCUMENTS

| | | |
|---|---|---|
| EP | 1961386 A1 | 8/2008 |
| EP | 2397097 B1 | 4/2014 |

(Continued)

OTHER PUBLICATIONS

International Search Report and Written Opinion for International application No. PCT/US2019/026506, dated Jul. 10, 2019, 11 pages.

*Primary Examiner* — Matthew J Kasztejna
(74) *Attorney, Agent, or Firm* — Seager, Tufte & Wickhem

(57) ABSTRACT

The present disclosure relates to the field of medical devices. Specifically, the present disclosure relates to devices, systems and methods for extending a working channel of an endoscope, such as for delivery of a stent.

8 Claims, 7 Drawing Sheets

(56) References Cited

U.S. PATENT DOCUMENTS

| | | | |
|---|---|---|---|
| 9,332,973 B2 | 5/2016 | McWeeney et al. | |
| 9,381,041 B2 | 7/2016 | Brown et al. | |
| 2003/0088153 A1* | 5/2003 | Carrillo, Jr. ....... | A61M 25/0075 600/114 |
| 2004/0260199 A1 | 12/2004 | Hardia, Jr. et al. | |
| 2006/0200041 A1 | 9/2006 | Weikel et al. | |
| 2007/0167868 A1 | 7/2007 | Sauer | |
| 2008/0242925 A1 | 10/2008 | Suda | |
| 2008/0243151 A1 | 10/2008 | Binmoeller et al. | |
| 2010/0191050 A1 | 7/2010 | Zwolinski | |
| 2013/0211433 A1* | 8/2013 | Kadykowski ......... | A61B 17/32 606/159 |
| 2016/0045100 A1 | 2/2016 | Eto | |
| 2017/0079628 A1 | 3/2017 | Mamiya | |

FOREIGN PATENT DOCUMENTS

| | | |
|---|---|---|
| EP | 2544763 B1 | 4/2016 |
| KR | 1020160137997 | 2/2016 |
| WO | 2008097949 A1 | 8/2008 |
| WO | 2010138277 A1 | 12/2010 |
| WO | 2015076154 A1 | 5/2015 |
| WO | 2016143204 A1 | 9/2016 |
| WO | 2016183485 A1 | 11/2016 |

\* cited by examiner

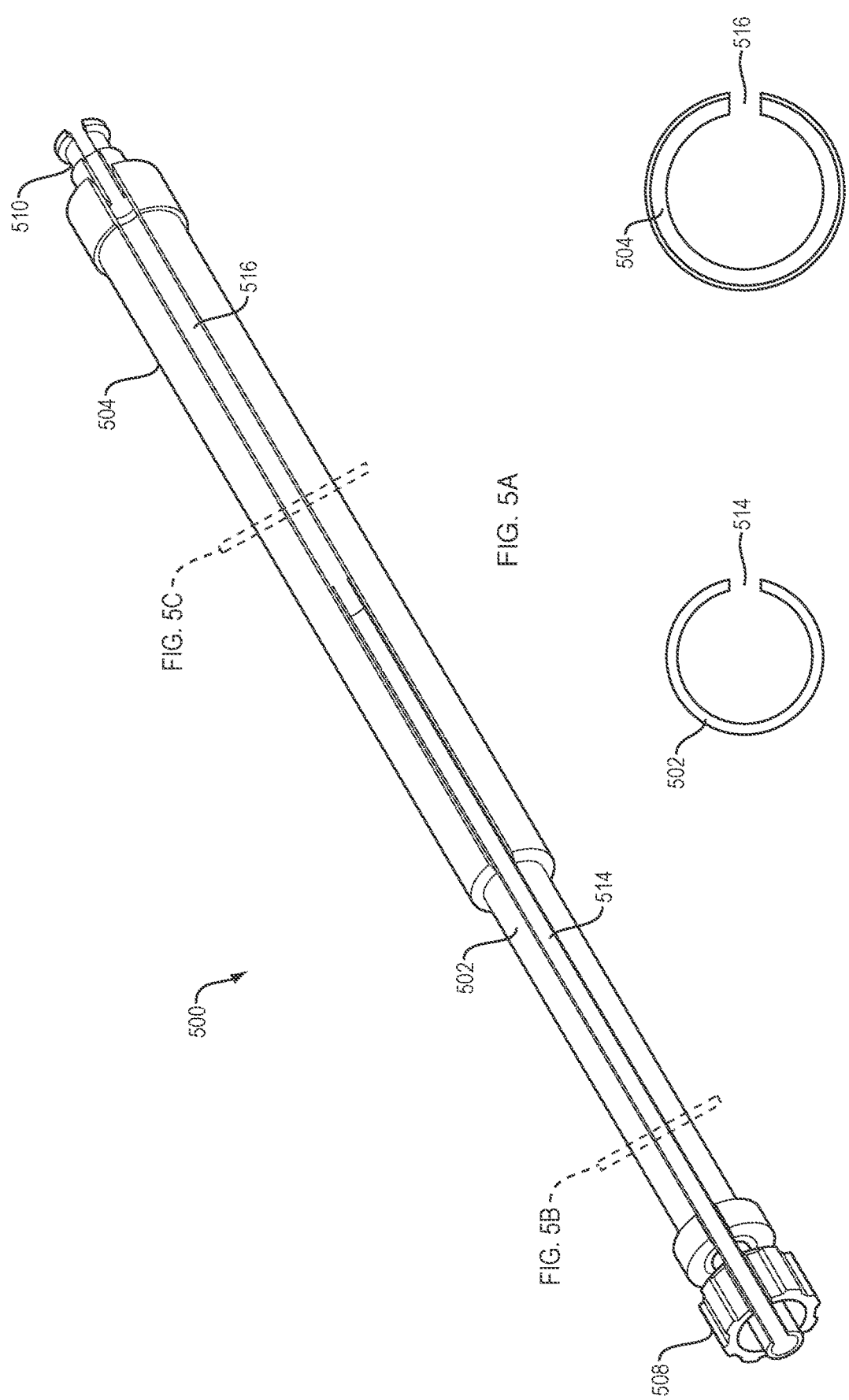

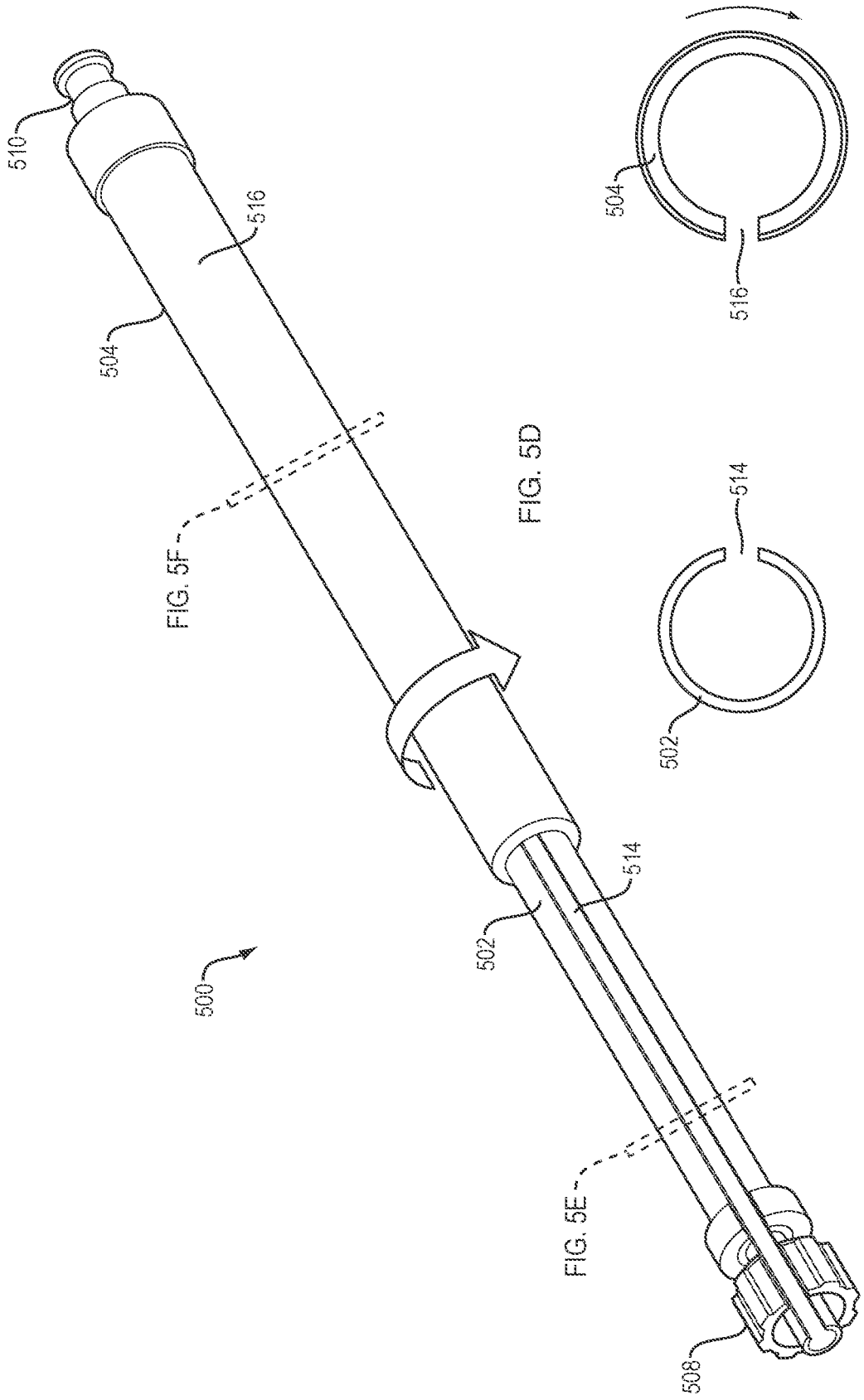

DEVICES AND METHODS FOR EXTENDING A WORKING CHANNEL

PRIORITY

This application is a division of U.S. Non-Provisional patent application Ser. No. 16/379,051, filed Apr. 9, 2019, which claims the benefit of priority under 35 USC § 119 to U.S. Provisional Patent Application Ser. No. 62/655,975, filed Apr. 11, 2018, which is incorporated by reference herein in its entirety and for all purposes.

FIELD

The present disclosure relates to the field of medical devices. Specifically, the present disclosure relates to devices, systems and methods for extending a working channel of an endoscope, such as for delivery of a stent.

BACKGROUND

Medical devices may include predetermined lengths for parts (e.g., a shaft of a delivery catheter, or the like) to reach into certain treatment sites within a patient and/or to be compatible with a specific auxiliary medical device (e.g., an endoscope). Production of these medical devices with predetermined shaft lengths may not work well with other patient treatment sites or with other auxiliary medical devices that they were not designed to be compatible with (e.g., other types of endoscopes or other patient body lumens). For example, a medical device may be attached to an endoscope that it was not designed to be compatible with, and a length of a shaft of the medical device (e.g., a delivery catheter) may extend too far distally out of a working channel of the endoscope, rendering the device and/or system not able to operate as intended, or incorporable entirely. For example, a distal tip of a catheter shaft that extends too far distally from the end of an echoendoscope may not be able to be imaged with ultrasound. Designing and producing multiple alternative medical devices with proper architecture to be compatible with different auxiliary medical devices may entail undue additional development and inventory costs. Additionally, there may be a loss of marketing appeal for having to purchase different versions of the same medical device simply to be compatible with multiple auxiliary devices.

It may therefore be desirable to have a device and/or system allowing for a medical device to be compatible with multiple auxiliary devices. It may also be desirable to ergonomically improve the medical device and/or system for a user operating the medical device and auxiliary device. It is with these considerations in mind that the improvements of the present disclosure may be advantageous.

SUMMARY

The present disclosure in various embodiments may include a device designed to connect to and work with an echoendoscope or other endoscopes. A shaft of a device may extend out of a distal end of the working channel of the echoendoscope a predetermined distance within a patient. This predetermined distance may be within a working range of the echoendoscope to display the treatment site to the user via ultrasound. A distal end length of the device that extends longer than this may be beyond the functioning range of the echoendoscope for the procedure, while an extended distal end length shorter than this may not allow for proper insertion, placement, and delivery of the stent.

The present disclosure in various embodiments includes devices, systems and methods for extending a working channel of an endoscope. In one aspect, an extension device may include a tubular inner member having a lumen extending therethrough. A tubular outer member may include a lumen extending therethrough. The lumen of the outer member may be configured to receive the inner member, the outer member and inner member may be slidable relative to each other in a telescoping fashion to a desired position that corresponds to an adjustable length of the device. A locking assembly may be configured to fix a relative position of the outer member and the inner member with respect to each other at the desired position. A proximal connector may be at a proximal end of the outer member and may be configured to connect to a distal end of a first medical device. A distal connector may be at a distal end of the inner member and may be configured to connect to a proximal end of a second medical device. The lumens of the inner member and the outer member may be coaxial. At least one of the proximal connector and the distal connector may be a luer lock connector. The plurality of desired positions may include three predetermined fixed positions. The fixed positions may include visual indicators on the inner or outer member, or both. The visual indicators may include markings. The fixed positions may include fasteners on one or both of the inner and outer members. The fasteners may include a first element on the inner member and a second element on the outer member. The first and second elements may be configured to mate with each other. The joint may pivot such that the first longitudinal axis is at an angle of 90 degrees to 180 degrees from the second axis. The locking assembly may be a detent. The locking assembly may be a screw. The screw may lock the outer member with respect to the inner member at the desired position by engaging the inner member.

In another aspect, an extension system may include an endoscope having a working channel. The system may include a delivery device. A shaft may extend distally from the delivery device and may be receivable within the working channel. The system may include an extension device. The extension device may include a tubular inner member that may have a lumen extending therethrough. The device may include a tubular outer member that may have a lumen extending therethrough. The lumen of the outer member may be configured to receive the inner member, the outer member and inner member may be slidable relative to each other in a telescoping fashion to a desired position that corresponds to an adjustable length of the extension device. The device may include a locking assembly configured to fix a relative position of the outer member and the inner member with respect to each other at the desired position. The device may include a proximal connector at a proximal end of the outer member configured to connect to a distal end of the delivery device. The device may include a distal connector at a distal end of the inner member configured to connect to a proximal end of the endoscope. The predetermined distance may be about 8 centimeters. The adjustable length may be a minimum of about 0 centimeters, and a maximum of about 8 centimeters. The lumens of the inner member and the outer member may be coaxial. The proximal connector may be a male luer connector and the distal connector may be a female luer connector. The desired position may include a plurality of predetermined fixed positions. The desired position may include three predetermined fixed positions. The joint may pivot such that the first longitudinal axis is at an angle of 90 degrees to 180 degrees from the second axis. The joint may include a spherical body at the distal portion of the inner member. The spherical body may have a first lumen therethrough that is in fluid communication with the inner lumen. A cupped body may be at the distal portion of the inner member and disposed about the spherical body. The cupped body may have a second lumen therethrough that is in fluid communication with the first lumen. The spherical body may be pivotable within the cupped body. The first lumen and the second lumen may be configured to accept the device. The locking assembly may be a protrusion on the inner member that corresponds to preset apertures in the outer member. The locking assembly may include a plurality of the preset apertures that may correspond to a plurality of the desired positions, which in turn may define a plurality of the adjustable lengths that are predetermined. The protrusion may include a compressible button, such that the button may be compressed to disengage the inner member from the outer member. The locking assembly may be a screw. The screw may lock the outer member with respect to the inner member at the desired position by engaging the inner member.

In another aspect, a method of extending a length of a working channel may include inserting an endoscope having a working channel therethrough into a patient. A catheter may be inserted into the patient through the working channel. An extension device may be placed having a lumen extending therethrough about a shaft of the catheter. The extension device may be attached to a proximal end of the working channel. The catheter may be attached to a proximal end of the extension device. The extension device may be adjusted to a desired position that corresponds to an adjustable length of the extension device. The extension device may be locked at the desired position. A tip of the catheter may be visualized using the endoscope. Placing the extension device about the shaft may be prior to inserting the catheter into the patient. The desired position may include at least one pre-determined fixed position of a locking assembly of the extension device configured to fix the adjustable length. The desired position may include a plurality of predetermined fixed positions. A plurality of channels of the extension device may be aligned with each other, such that the extension device may be placed and removed from about the shaft. The extension device may be rotated between an open configuration with the channels substantially aligned, and a closed configuration with the channels not substantially aligned.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 5A through 5C illustrate an extension device having an inner and an outer channel in an open configuration, in accordance with an embodiment of the present disclosure.

FIGS. 5D through 5F illustrate the extension device of FIGS. 5A through 5C in a closed configuration.

DETAILED DESCRIPTION

Figure 1:
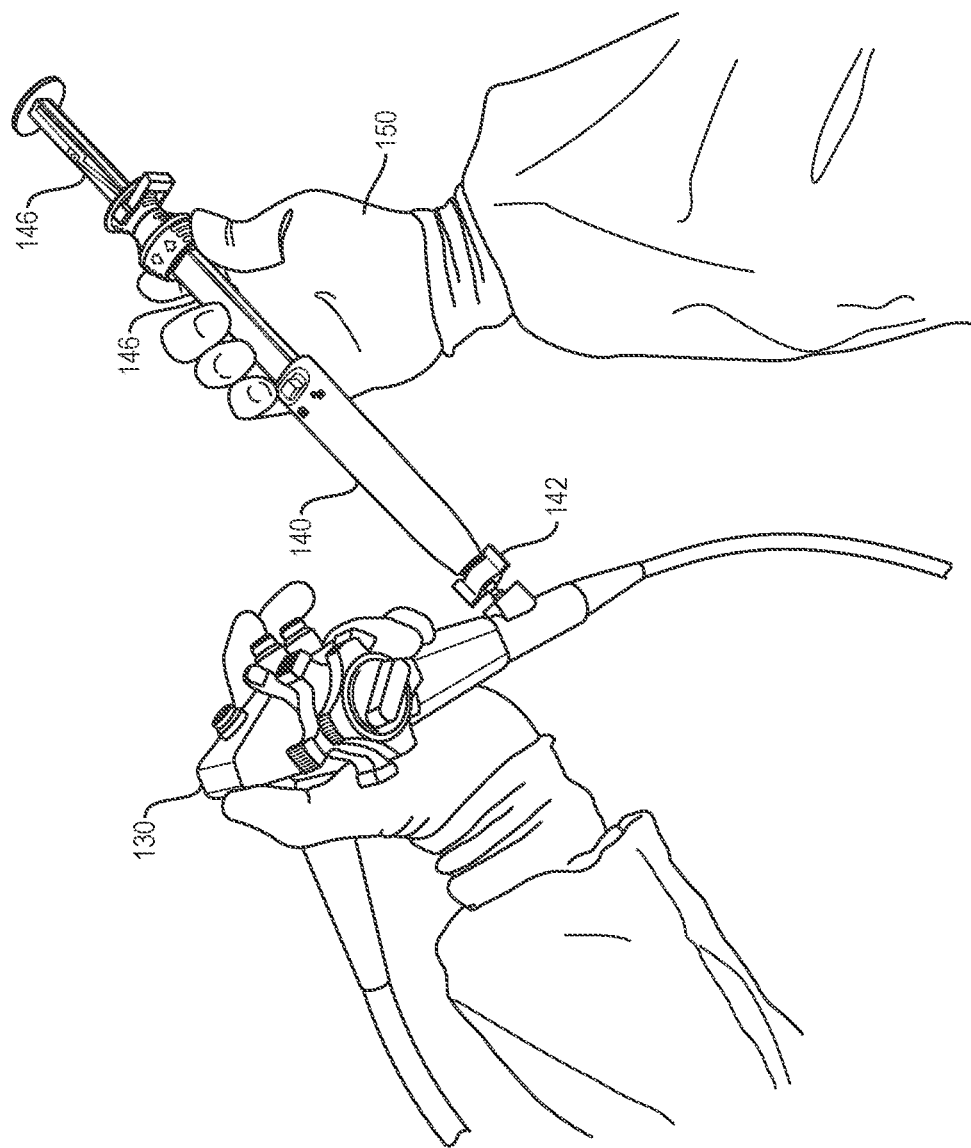
FIG. 1 illustrates an example of a user operating a medical device with a fixed length connected to an endoscope.

The present disclosure is not limited to the particular embodiments described. The terminology used herein is for the purpose of describing particular embodiments only, and is not intended to be limiting. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

As used herein, the term "distal" refers to the end farthest away from the medical professional when introducing a device into a patient, while the term "proximal" refers to the end closest to the medical professional when introducing a device into a patient.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

Embodiments of the present disclosure include devices and systems, and methods used to extend a working channel. Medical devices (e.g., a catheter) that may be designed to extend to certain treatment sites of a patient and/or to be compatible with a specific auxiliary medical device (e.g., an endoscsope) may be used with extension devices of the present disclosure in order to reach into other treatment sites and/or to be compatible with other auxiliary medical devices.

Using an echoendoscope, as an example, a delivery catheter may be used for delivering a self-expanding drainage stent. The stent delivery device may be designed to connect to and work with an echoendoscope. Placement of a drainage stent within the body may be performed by insertion of a catheter carrying the stent under ultrasound guidance. The catheter is passed through the wall of a first body lumen (e.g., gastrointestinal tract) into an adjacent lumen (e.g., pseudocyst) and a distal retention member of the stent is deployed. The catheter may then be retracted and a proximal retention member deployed within the GI tract (e.g., stomach). Such an ultrasonic procedure may be performed using an echoendoscope in which a shaft of the delivery device is inserted through the echoendoscope. The working channel of an echoendoscope typically has a specific length, e.g., about 125 cm to about 130 cm, and a delivery catheter or device will typically extend through the length of the working channel with a shaft length of about 137 cm to about 138 cm such that about 8 cm of a distal end of the catheter will extend out of a distal end of the working channel a predetermined distance within the patient. This predetermined distance may be within the working range of the echoendoscope to display the treatment site, including the catheter tip and stent, to the user via ultrasound. A distal end length of the catheter that extends longer than this may be beyond the functioning range of the echoendoscope for the procedure, while an extended distal end length shorter than this may not allow for proper insertion, placement, and delivery of the stent.

With reference to FIG. 1, an example of a device and echoendoscope in accordance with the above description for delivery of a drainage stent is illustrated. The device 140 is connected to an echoendoscope 130 for operation by a user 150. The device 140 is connected to the echoendoscope 130 via a connector 142 that is a luer lock fitting, causing the device 140 to be in a locked position with respect to the echoendoscope 130. The user 150 may operate the echoendoscope 130 with one hand while operating the device 140 with the other hand. A shaft of the device 140 extends through a working channel of the echoendoscope 130 and extends from a distal end of the echoendoscope 130 a predetermined distance. The device 140 is in the locked position with the echoendoscope 130 and has a set shaft length such that the predetermined distance does not vary in a proximal or distal direction through movement of the device 140 with respect to the echoendoscope by the user. The handles 146 of the device 140 may be actuated in sequence during a procedure to deliver a stent while visualizing the distal tip of the shaft of the device with the echoendoscope.

A medical professional may desire to use a medical device designed for a particular auxiliary medical device (e.g., an echoendoscope) having a given working channel length, with a different auxiliary medical device (e.g., a direct imaging endoscope or different brand or configuration of endoscope) having a different working channel length. Should professional user connect the device to the different auxiliary device, the functioning parts of the device (e.g., the length of the catheter shaft) may fail the needs of the procedure. For example, the distance that the medical device extends from a distal end of a working channel of a different auxiliary device may vary with the different lengths of the various auxiliary devices. For example, it may be necessary or desirable for the medical device to be locked to the endoscope, e.g., so that it is capable of being manipulated along with the endoscope by a single hand of the user, or so that the medical device cannot be partially or inadvertently withdrawn or extended from the endoscope to maintain a desired predetermined distance of extension beyond the working channel.

Figure 2:
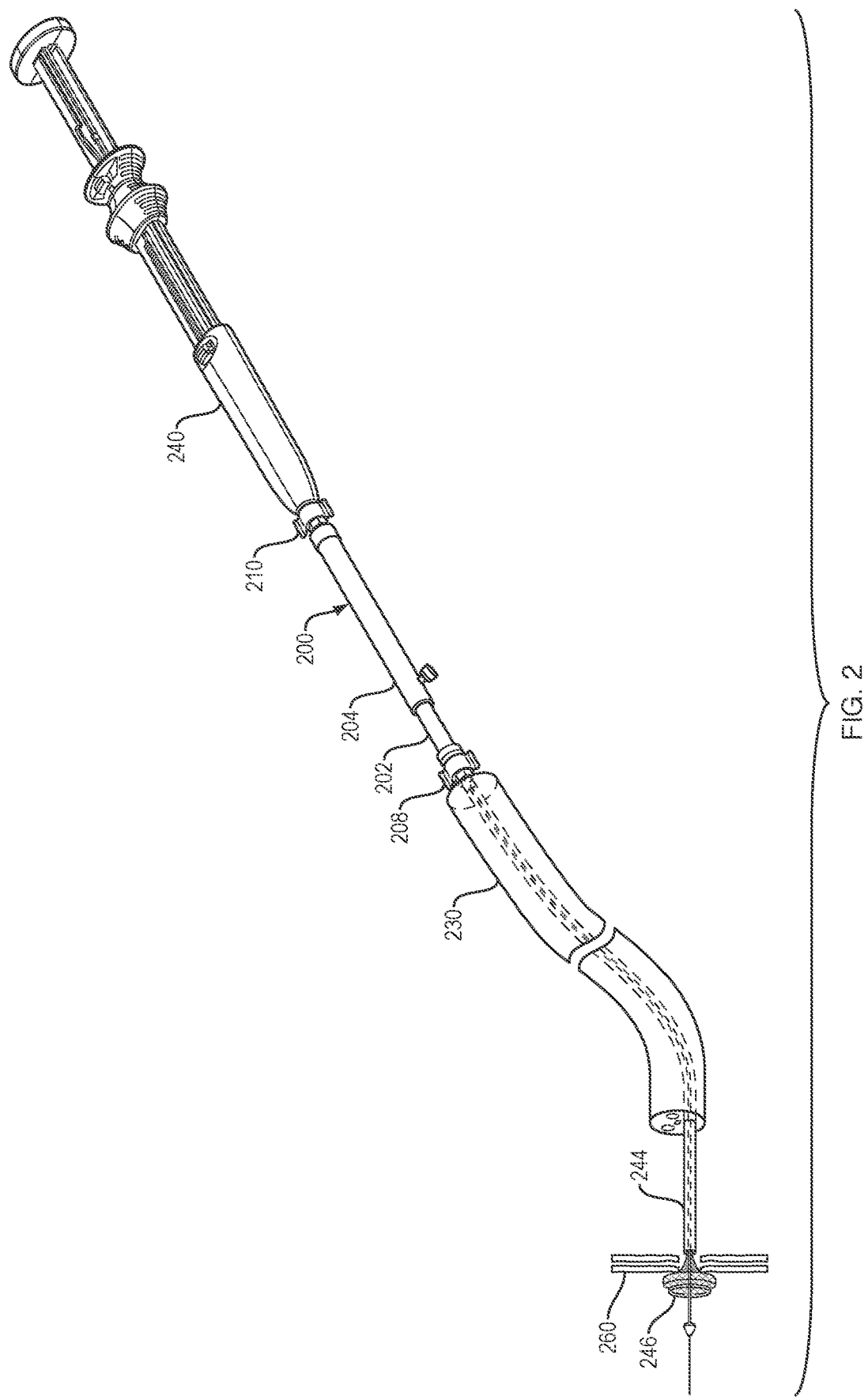
FIG. 2 illustrates a medical device, an extension device, and an endoscope connected in series while delivering a stent, in accordance with an embodiment of the present disclosure.

With reference to FIG. 2, an embodiment of a system for extending a working channel according to the present disclosure is illustrated, which includes an endoscope 230 inserted into a patient having a working channel through the endoscope 230 for devices to be passed through. An exemplary stent delivery device 240, shown here for purposes of illustration, as an AXIOS™ device manufactured by Boston Scientific Corporation, includes a distal end with a shaft 244 extending distally therefrom. The shaft 244 is receivable within the working channel. The shaft 244 is depicted delivering a stent 246 to target tissue 260 of the patient. An extension device extending between the delivery device and the endoscope allows for delivery device 240 to maintain the shaft 244 at a predetermined distance from the distal end of the endoscope 230. The extension device 200 is attached between the delivery device 240 and the endoscope 230. The extension device 200 has a tubular inner member 202 including a lumen extending therethrough. The extension device 200 also has a tubular outer member 204 including a lumen extending therethrough. The lumen of the outer member 204 is configured to receive the inner member 202. The outer member 204 and inner member 202 are slidable relative to each other in a telescoping fashion to a desired position that corresponds to an adjustable length of the extension device 200. A proximal connector at a proximal end of the outer member 204 is configured to connect to a connector 210 at a distal end of the handle of the delivery device 240. A distal connector 208 at a distal end of the inner member is configured to connect to a proximal end of the endoscope 230. The adjustable length of the device 200 is such that the shaft 244 is extendable through the lumen of the outer member 204 and inner member 202 of the extension device 200, through the working channel from the proximal end to a distal end of the endoscope 230, and beyond the distal end of the endoscope 230 a predetermined distance.

In various embodiments described here or otherwise within the scope of the present disclosure, the predetermined distance of the shaft from the distal end of the endoscope may be, e.g., in the range of about 7.5 cm to about 8.5 cm. An extension device may be removable from about the shaft of the auxiliary medical devices, such as an endoscope and a delivery device, without withdrawing the shaft proximally through the lumens of the inner and outer members of the extension device. The adjustable length of the extension device may be, e.g., a minimum of about 0 centimeters and a maximum of about 3 centimeters, or a minimum of about 0 centimeters and a maximum of about 8 centimeters. The lumens of the inner member and the outer member may be coaxial. The lumen of the inner member may have a diameter that substantially matches a diameter of a working channel of an endoscope. The lumen of the outer member may have a lumen that substantially matches an outer diameter of the inner member. The extension device may include a locking assembly, such as the set screw shown in FIG. 2, to fix the outer member 204 and inner member 202 with respect to each in a desired position that corresponds to an adjustable length of the extension device 200. A locking assembly of an extension device may have a pre-determined fixed position coinciding with a length of the shaft (e.g., a catheter) of a medical device between a proximal end of the endoscope and a distal end of the medical device (e.g., a delivery device).

Figure 3:
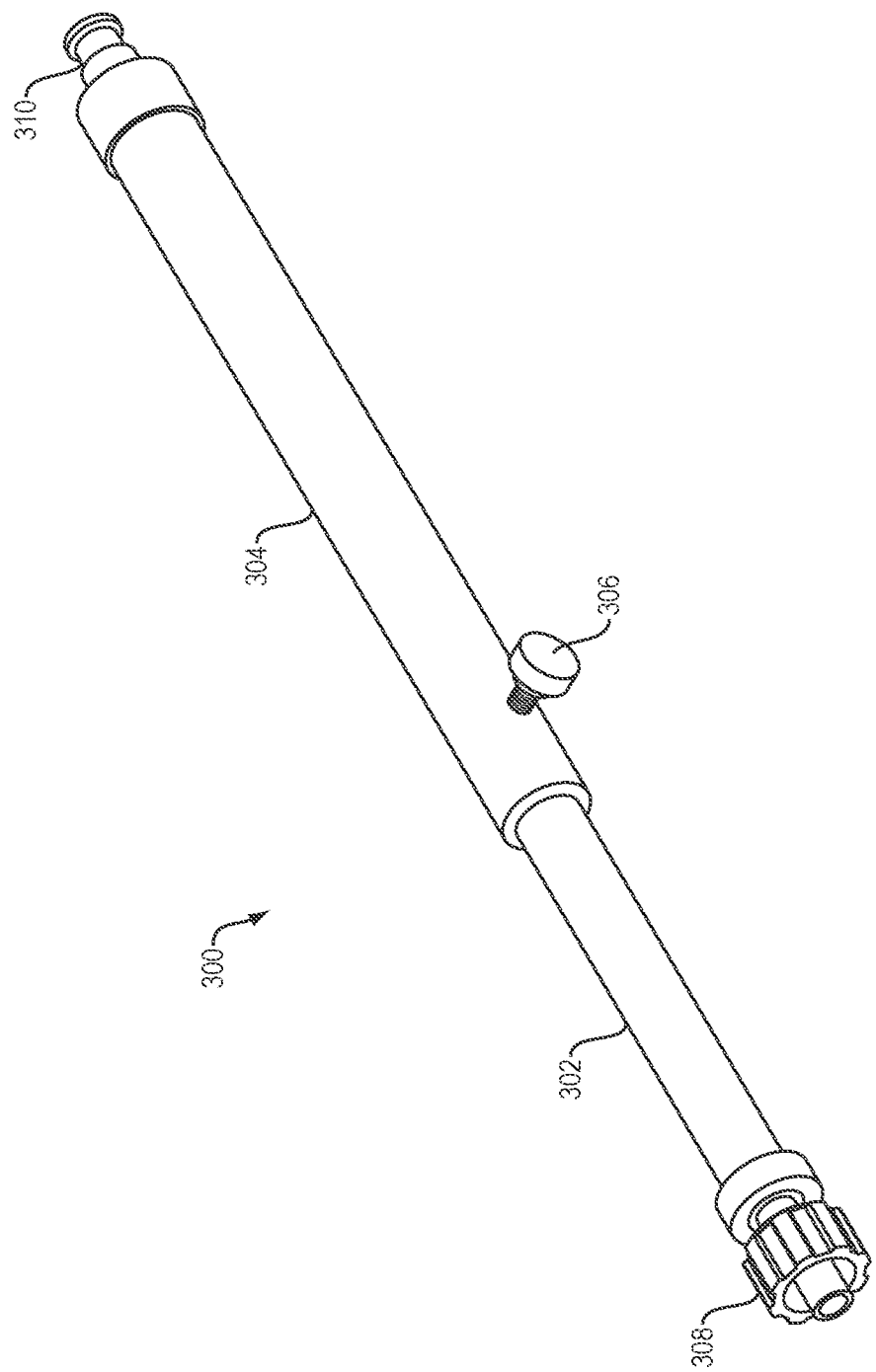
FIG. 3 illustrates a perspective view of an extension device, in accordance with an embodiment of the present disclosure.

With reference to FIG. 3, an embodiment of an extension device for extending a working channel according to the present disclosure is illustrated. Extension device 300 has a tubular inner member 302 including a lumen extending therethrough. The device 300 also includes a tubular outer member 304 having a lumen extending therethrough, which is configured to receive the inner member 302. The lumen of the outer member 304 may have a diameter that substantially matches the outer diameter of the inner member 302. The outer member 304 and inner member 302 are slidable relative to each other in a telescoping fashion to a desired position that corresponds to an adjustable length of the device 300. A locking assembly 306 (e.g., a screw or the like) is configured to fix a relative position of the outer 304 member and the inner member 302 with respect to each other at the desired position. The locking assembly 306 locks the outer member 304 with respect to the inner member 302 at the desired position by engaging the inner member 302. The locking assembly 306 shown in FIGS. 2-3, includes a knobbed screw that is disposed through an aperture of the outer member 304. A user may tighten the knobbed screw such that it engages and locks the inner member 302 with respect to the outer member 304. A proximal connector 310 (e.g., a luer-lock connector) at a proximal end of the outer member 304 is configured to connect to a distal end of a first medical device (e.g., a stent delivery device). A distal connector 308 (e.g., a female luer-lock connector) at a distal end of the inner member 302 is configured to connect to a proximal end of a second medical device (e.g., an endoscope).

Figure 4:
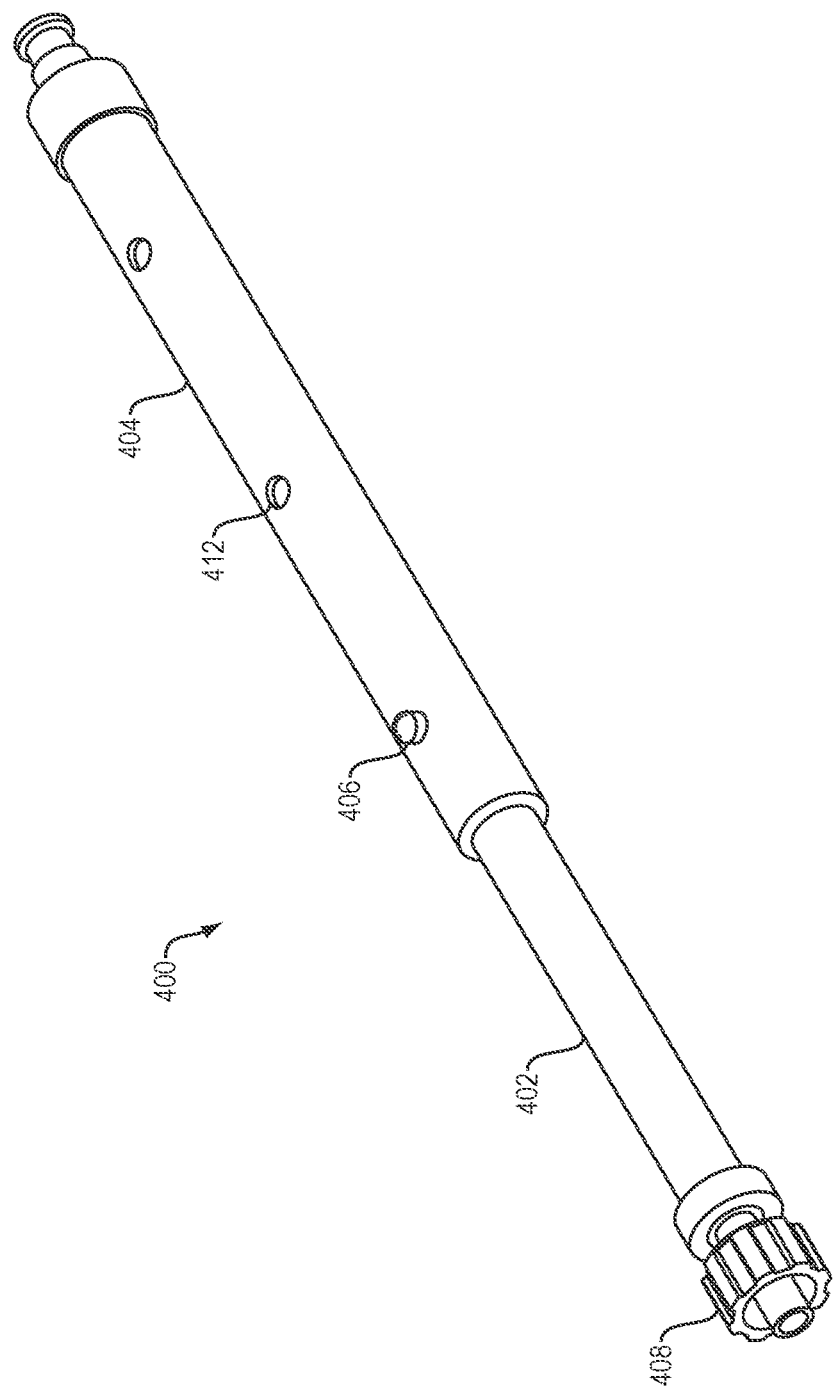
FIG. 4 illustrates a perspective view of an extension device having pre-determined locking positions, in accordance with an embodiment of the present disclosure.

With reference to FIG. 4, an embodiment of a device for extending a working channel according to the present disclosure is illustrated, which includes an extension device 400 with a locking assembly. The locking assembly includes a protrusion 406 (e.g., a compressible button, a detent, or the like) on the inner member 402 that corresponds to preset apertures 412 in the outer member 404. The protrusion 406 can be compressed radially such that it completely enters and clears the inner surface of the lumen of the outer member 404, disengaging the inner member 402 from the apertures 412 of the outer member 404. This allows the inner member 402 and the protrusion 406 to slide with respect to the outer member 404, resulting in an adjustment of the overall length of the device 400. In some embodiments, the locking assembly 406 may include a plurality of preset apertures 412 that correspond to a plurality of desired positions. The numerous positions of the locking assembly 406 may define predetermined adjustable lengths of the device 400. For example, the apertures 412 and desired positions may correspond to known lengths required for use with an assortment of auxiliary devices such as endoscopes having different lengths of working channels. Each aperture 412 may correspond to a type of auxiliary device. The protrusion 406 may engage the aperture 412 corresponding to the auxiliary device being used to achieve the appropriate adjustable length of the device 400. An appropriate adjustable length of the device 400 may be such that a shaft extends through the device 400 with only a predetermined length of the shaft extending from the distal end of the auxiliary device. For example, FIG. 4 illustrates three apertures 412 corresponding to three predetermined fixed positions of the inner member 402 with respect to the outer member 404 of the device. Thus, in this embodiment the example of three fixed positions correspond to three predetermined adjustable lengths of the extension device that will shorten the effective length of the shaft by the amount of the adjustable length of the extension device. Visual indicators, such as markings, may be on the inner and/or outer member that correspond to the desired positions. As an alternative to protrusions and apertures, in other embodiments, one or both of the inner and outer members may include fasteners that may have a first element on the inner member and a second element on the outer member configured to mate with each other.

With reference to FIGS. 5A through 5F, an embodiment of a device for extending a working channel according to the present disclosure is illustrated, which includes a channel 514 extending along an inner member 502, along a distal connector 508, and through to a lumen of the inner member 502. A channel 516 extends along the outer member 504, along the proximal connector 510, and through to the lumen of the outer member 504. The channels 514 and 516 of the inner member 502 and outer member 504 are configured to align with each other. When the channels 514 and 516 are aligned, the device 500 may be placed and removed from about a shaft of a medical device extending through the lumens of the inner member 502 and outer member 504 of the extension, including without having to proximally withdraw the shaft medical device from the extension device. One or both of the outer member 504 and the inner member 502 are rotatable with respect to each other. The device may be transitioned between an open configuration (e.g., as illustrated in FIGS. 5A-5C) with the channel 514 and channel 516 substantially aligned, and a closed configuration (e.g., as illustrated in FIGS. 5D-5F) with the channel 514 and channel 516 not substantially aligned. When the device 500 is in the closed position with a shaft extending through the inner member 502 and the outer member 504, the device 500 and shaft are secure such that they cannot be separated from each other, other than to remove the shaft proximally through the inner member 502 and outer member 504. When the device 500 is in the open position with the shaft disposed through the inner member 502 and the outer member 504, the device 500 may be removed from about the shaft in a substantially radial direction with respect to a longitudinal axis extending along the length of the channels 514 and 516. In various embodiments, described here or otherwise within the scope of the present disclosure, the one or more channels 514 and/or 516 extending along the distal connector 508 and/or the proximal connector 510 may instead be perforated material, weakened material, and/or thinner material than the remainder of the connector 508 and/or 510. Alternatively, the connector 508 and/or 510 may be made entirely of a material that is destructible by deliberate force of the user pulling or stripping the extension device 500 off of the shaft. Such embodiments may allow for the device 500 to be removed from an endoscope, and/or a shaft of a medical device without removing other parts of the system first. Such embodiments may also allow for the device 500 to be removed more rapidly compared to removing other auxiliary devices or other medical devices of the system before removing the extension device 500.

In various embodiments described here or otherwise within the scope of the present disclosure, the inner member and outer member may comprise various polymer and/or metallic materials. Materials may include stainless steel, aluminum, polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex® high-density polyethylene, Marlex® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, and/or polyvinylidene chloride (PVdC). Materials may be selected to withstand forces associated with advancement and withdrawal of medical devices and endoscopes within the patient.

Figures 6A, 6B:
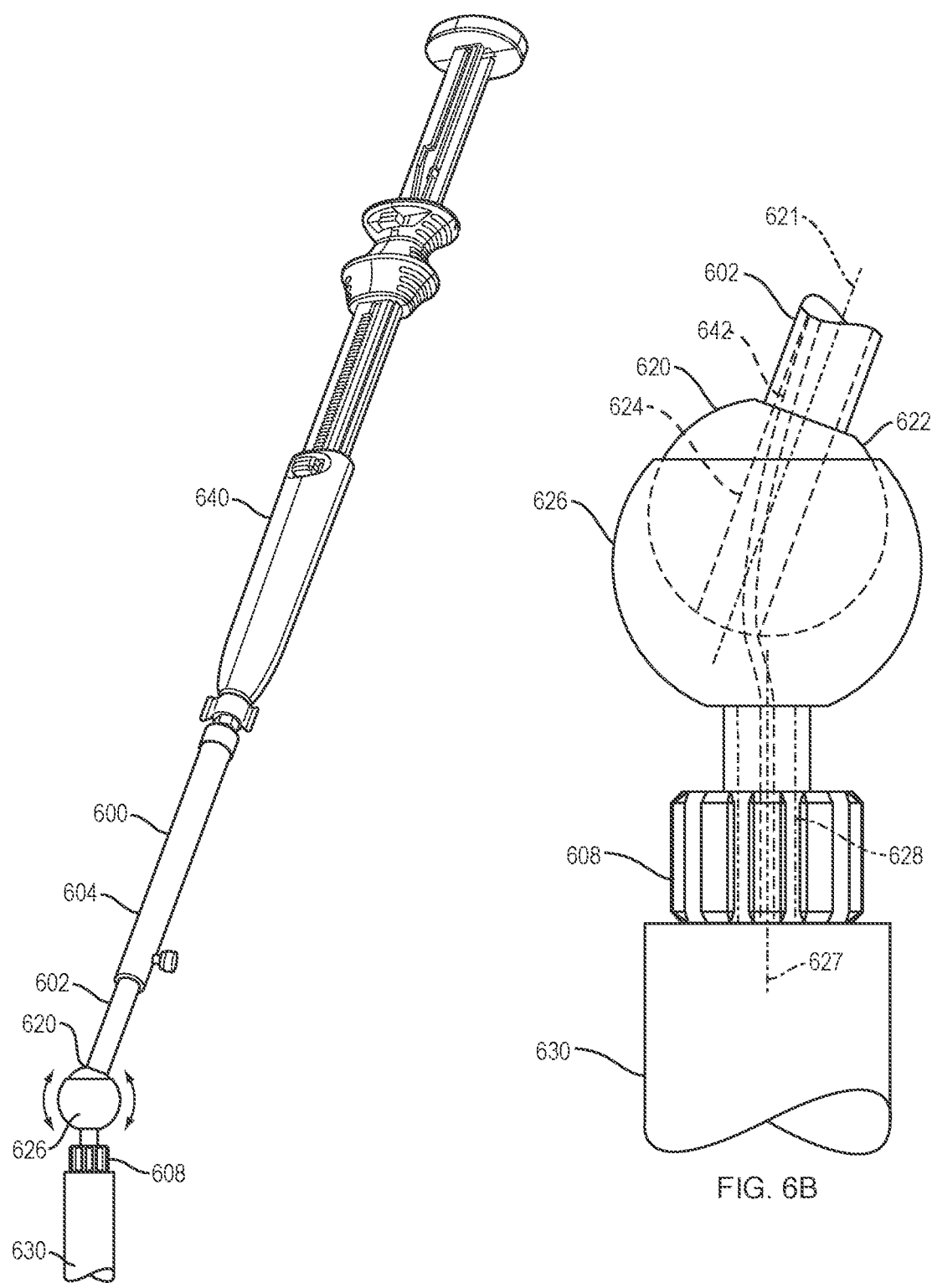
FIG. 6A illustrates an extension device having a pivotable joint, in accordance with an embodiment of the present disclosure.
FIG. 6B illustrates a section of the device of FIG. 6A.

With reference to FIGS. 6A and 6B, an embodiment of a device for extending a working channel according to the present disclosure is illustrated, which includes a pivotable joint 620 disposed at a distal portion of an inner member 602 of the device 600. The device 600 extends the working channel of an endoscope 630 to be compatible with the shaft of the medical device 640, such that the shaft may extend a predetermined distance beyond the distal end of the endoscope. The pivotal joint 620 is proximal to a distal connector 608 that connects the device 600 to the endoscope 630. The joint 620 has a first longitudinal axis 627 that is alignable with a longitudinal axis of the endoscope 630 and a portion of the inner member 602 distal to the pivotal joint. The joint 620 also has a second longitudinal axis 621 that is alignable with a longitudinal axis of a remaining portion of the inner member 602. The joint 620 comprises a spherical body 622 at a distal portion of the inner member 602 that is proximal to the distal connector 608. The spherical body 620 has a lumen 624 therethrough that is in fluid communication with the lumen of the inner member 602. The joint 620 also includes a cupped body 626 at the distal portion of the inner member 602 that is proximal to the distal connector 608. The cupped body 626 is disposed about the spherical body 620. The cupped body 626 has a lumen 628 therethrough that is in fluid communication with the lumen 624 of the spherical body 622. The spherical body 620 is pivotable within the cupped body 626 while maintaining the lumens of the inner member 602, spherical body 622, and cupped body 626 in fluid communication. A shaft 642 of the medical device 640 is extendable through the lumens 624 and 628 of the joint 620. The joint 620 may pivot such that the first longitudinal axis 627 is at an angle of about 90 degrees to about 180 degrees from the second axis 621. A user may benefit from the pivotable joint 620 because it may allow for the medical device 640 and the device 600 to freely move angularly with respect to the cupped body 626 and the endoscope 630. The second axis 621 has freedom to move 360 degrees in any plane from 90 degrees (perpendicular to the first axis 627) to 180 degrees (parallel to the first axis 627). This may ergonomically assist the user during a procedure. There may be more freedom and comfort for the user operating the medical device 640 and endoscope 630 than that of other embodiments where the medical device, extension device, and endoscope are locked together in one position that cannot be pivoted with respect to each other.

In various embodiments described here or otherwise within the scope of the present disclosure, the proximal and/or distal connector may be a male or female luer fitting. The one or more connectors may include a rotating luer nut and/or a winded luer fitting. The connectors may removably connect and tighten to a variety of endoscopes and medical devices.

In various embodiments described here or otherwise within the scope of the present disclosure, the locking assembly may comprise a quick release locking nut, a twist frictional fit lock, a slotted fit lock, a button fit lock, a detent lock, or the like.

In various embodiments described here or otherwise within the scope of the present disclosure, the extension device may be a tubular member of a length corresponding to an endoscope such that a shaft of a catheter extends distally from the endoscope a predetermined distance. The tubular member may have a proximal connector at a proximal end of the member that is configured to connect to a distal end of a medical device. The tubular member may have a distal connector at a distal end of the member that is configured to connect to a proximal end of an endoscope.

In various embodiments, a method of extending a length of a working channel may include inserting an endoscope having a working channel into a patient. A catheter may be inserted into the patient through the working channel. An extension device may have a lumen extending therethrough about a shaft of the catheter. The extension device may be attached to a proximal end of the working channel. The catheter may be attached to a proximal end of the extension device. The extension device may be adjusted to a desired position that corresponds to an adjustable length of the extension device. The extension device may be locked at the desired position. The extension device may be adjusted to a desired position such that a distal tip of the catheter extends at most about 8 cm from a distal end of the endoscope. A tip of the catheter may be visualized using the endoscope. The extension device may be removed from the endoscope and from about a shaft of the catheter while the catheter remains within the working channel of the endoscope. The placing step may include placing the extension device about the shaft after inserting a catheter into the patient. The placing step may include placing the extension device about the shaft prior to inserting a catheter into the patient. The desired position may include at least one pre-determined fixed position of a locking assembly of the extension device configured to fix the adjustable length. The desired position may include a plurality of predetermined fixed positions. A plurality of channels of the extension device may be aligned with each other, such that the extension device may be placed and removed from about the shaft of the catheter. The extension device may be transitioned between an open configuration with the channels substantially aligned, and a closed configuration with the channels not substantially aligned.

All of the devices and/or methods disclosed and claimed herein can be made and executed without undue experimentation in light of the present disclosure. While the devices and methods of this disclosure have been described in terms of certain embodiments, it may be apparent to those of skill in the art that variations can be applied to the devices and/or methods and in the steps or in the sequence of steps of the methods described herein without departing from the concept, spirit and scope of the disclosure. All such similar substitutes and modifications apparent to those skilled in the art are deemed to be within the present disclosure.

What is claimed is:

1. An extension device, comprising:
a tubular inner member including a lumen extending therethrough;
a tubular outer member including a lumen extending therethrough, the lumen of the outer member configured to receive the inner member, the outer member and inner member slidable relative to each other in a telescoping fashion to a desired position that corresponds to an adjustable length of the extension device;
a locking assembly configured to fix the outer member and the inner member with respect to each other at the desired position;
a proximal connector at a proximal end of the outer member configured to connect to a distal end of a handle of a first medical device;
a distal connector at a distal end of the inner member configured to connect to a proximal end of a second medical device;
a channel extending along the inner member, the distal connector, and through to the lumen of the inner member;
a channel extending along the outer member, the proximal connector, and through to the lumen of the outer member, and
wherein the extension device is configured to facilitate an extension of the first medical device therethrough such that the first medical device extends beyond a distal end of the second medical device to deliver a stent from a distal end of a shaft extending distally from the handle of the first medical device;
wherein the extension device is removable from about the shaft of the first medical device without drawing the shaft proximally through the lumens of the inner and outer members; and
wherein the channels of the inner and outer member are configured to align with each other, such that the extension device may be placed and removed from about the shaft of the first medical device.

2. The extension device of claim 1, wherein the shaft of the first medical device is extendable through the lumen of the outer and inner members of the extension device, through a lumen extending from the proximal end to a distal end of the second medical device, and beyond the distal end of the second medical device a predetermined distance.

3. The extension device of claim 1, wherein the desired position includes at least one predetermined fixed position of the locking assembly.

4. The extension device of claim 1, wherein one or both of the outer member and the inner member are rotatable with respect to each other, such that the device may be transitioned between an open configuration with the channel of the inner member and the channel of the outer member substantially aligned, and a closed configuration with the channel of the inner member and the channel of the outer member not substantially aligned.

5. An extension system, comprising:
an endoscope having a working channel;
a delivery device having a shaft extending distally from the delivery device and receivable within the working channel; and
an extension device comprising:
a tubular inner member including a lumen extending therethrough;
a tubular outer member including a lumen extending therethrough, the lumen of the outer member configured to receive the inner member, the outer member and inner member slidable relative to each other in a telescoping fashion to a desired position that corresponds to an adjustable length of the extension device;
a locking assembly configured to fix the outer member and the inner member with respect to each other at the desired position;
a proximal connector at a proximal end of the outer member configured to connect to a distal end of a handle of the delivery device;
a distal connector at a distal end of the inner member configured to connect to a proximal end of the endoscope;
a channel extending along the inner member, the distal connector, and through to the lumen of the inner member; and
a channel extending along the outer member, the proximal connector, and through to the lumen of the outer member, wherein the channels of the inner and outer member are configured to align with each other, such that the extension device may be removed from about the shaft of the delivery device while the shaft is in the working channel;
wherein the delivery device is configured to extend through and beyond a distal end of the endoscope to deliver a stent from a distal end of the delivery device; and
wherein the extension device is removable from about the shaft of the delivery device without withdrawing the shaft proximally through the lumens of the inner and outer members.

6. The system of claim 5, wherein the adjustable length of the extension device is such that the shaft is extendable through the lumen of the outer and inner members of the extension device, through the working channel extending from the proximal end to a distal end of the endoscope, and beyond the distal end of the endoscope a predetermined distance.

7. The system of claim 5, wherein the locking assembly has a predetermined fixed position coinciding with a length of the shaft between the proximal end of the endoscope and the distal end of the delivery device.

8. The system of claim 5, wherein one or both of the outer member and the inner member are rotatable with respect to each other, such that the extension device may be transitioned between an open configuration with the channel of the inner member and the channel of the outer member substantially aligned, and a closed configuration with the channel of the inner member and the channel of the outer member not substantially aligned.

* * * * *